(12) United States Patent
Miller et al.

(10) Patent No.: US 8,418,300 B2
(45) Date of Patent: Apr. 16, 2013

(54) RECIPROCATING WORKPIECE DEVICE WITH A DRIVE SYSTEM SEEKING THE RESONANCE OF THE DRIVEN SYSTEM PORTION THEREOF

(75) Inventors: Kevin A. Miller, Bellevue, WA (US); John W. Pace, Bothell, WA (US); Wolter F. Benning, Seattle, WA (US); Patrick A. Headstrom, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 805 days.

(21) Appl. No.: 11/993,744

(22) PCT Filed: Jun. 30, 2006

(86) PCT No.: PCT/IB2006/052214
§ 371 (c)(1),
(2), (4) Date: Apr. 9, 2010

(87) PCT Pub. No.: WO2007/004180
PCT Pub. Date: Jan. 11, 2007

(65) Prior Publication Data
US 2010/0186179 A1   Jul. 29, 2010

Related U.S. Application Data

(60) Provisional application No. 60/695,659, filed on Jun. 30, 2005.

(51) Int. Cl.
*A61C 17/34* (2006.01)

(52) U.S. Cl.
USPC .............................................. 15/22.1; 15/22.2

(58) Field of Classification Search .................. 15/22.2, 15/22.1, 22.3, 22.4, 23, 24
See application file for complete search history.

(56) References Cited

U.S. PATENT DOCUMENTS

| | | | |
|---|---|---|---|
| 4,146,020 A | | 3/1979 | Moret et al. |
| 5,378,153 A | | 1/1995 | Giuliani et al. |
| 5,613,259 A | | 3/1997 | Craft et al. |
| 5,784,742 A | * | 7/1998 | Giuliani et al. ................. 15/22.1 |
| 6,140,723 A | * | 10/2000 | Matsui et al. .................... 310/81 |
| 6,463,740 B1 | * | 10/2002 | Schmidt et al. ................. 60/772 |
| 6,808,331 B2 | * | 10/2004 | Hall et al. ...................... 401/146 |
| 6,859,968 B2 | | 3/2005 | Miller et al. |
| 2002/0084707 A1 | | 7/2002 | Tang |

FOREIGN PATENT DOCUMENTS

| | | |
|---|---|---|
| WO | 03092535 A2 | 11/2003 |
| WO | 04000156 A1 | 12/2003 |

* cited by examiner

*Primary Examiner* — Shay Karls

(57) ABSTRACT

A workpiece system with a reciprocating motion which includes a motor assembly for producing an output drive signal with a periodic force pulse. The drive signal is coupled to a driven member assembly through a magnetic arrangement, wherein the driven member assembly has a workpiece mounted thereon with a return spring assembly. The driven member assembly has a resonant mechanical frequency. As the RPM of the motor increases from zero following startup, the drive signal frequency increases to the point very near resonance, where the energy from the drive signal is transferred into the reciprocating motion of the driven assembly, producing an effective amplitude of workpiece motion.

29 Claims, 9 Drawing Sheets

RECIPROCATING WORKPIECE DEVICE WITH A DRIVE SYSTEM SEEKING THE RESONANCE OF THE DRIVEN SYSTEM PORTION THEREOF

CROSS REFERENCE TO RELATED APPLICATION

This application claims the benefit of U.S. provisional application Ser. No. 60/695,659 filed Jun. 30, 2005, which is incorporated herein by reference.

TECHNICAL FIELD

This invention relates generally to power devices having a reciprocating workpiece, such as a power toothbrush, which operate at or near resonance, and more particularly concerns such a device which includes a drive system which seeks the resonant frequency of an associated reciprocating driven system.

BACKGROUND OF THE INVENTION

Resonant operation is useful and desirable for power devices having workpieces with reciprocating motion, due to the inherent efficiency of such devices when they are operating at or near resonance. In such a case, the driven assembly/system portion of the device which includes the workpiece is driven at or near its resonant frequency. This requires matching substantially the drive frequency of the drive system portion of the device to the resonant frequency of the driven system portion of the device. The workpiece can include, besides toothbrushes, shavers, sanders, power knives and other reciprocating tools.

In those products which are mass-produced, the tolerances of the resonant system (the driven system) must be carefully controlled. Tuning of the devices during assembly, or by using an adaptive drive system, is necessary but is typically tedious and expensive, increasing costs and raising quality control issues. Accordingly, while resonant operation is often an advantage, it is typically designed out of such devices to reduce manufacturing costs. Non-resonant systems, on the other hand, usually have problems of efficiency at relatively high operating speeds, as well as high noise levels, due to the normal operation of the drive train portion of such systems.

It is thus desirable to have a power device with a reciprocating workpiece which includes a drive system/driven system combination which operates at resonance but without the strict operating tolerances for the driven system otherwise required.

SUMMARY OF THE INVENTION

Accordingly, the present invention is a workpiece system having a reciprocating action, comprising: a drive assembly producing an output drive signal comprising periodic force pulses, resulting in a drive frequency which increases from zero in operation of the drive assembly; and a driven member assembly having a workpiece mounted thereon with a return spring assembly, the driven member assembly having a resonant frequency, wherein, as the drive frequency increases from zero, it will approach the resonant frequency of the driven assembly, wherein at approximately said resonant frequency, at least a substantial portion of energy produced by the motor assembly is transferred into the movement of the workpiece, producing an effective workpiece action.

BEST MODE FOR CARRYING OUT THE INVENTION

Figure 1:
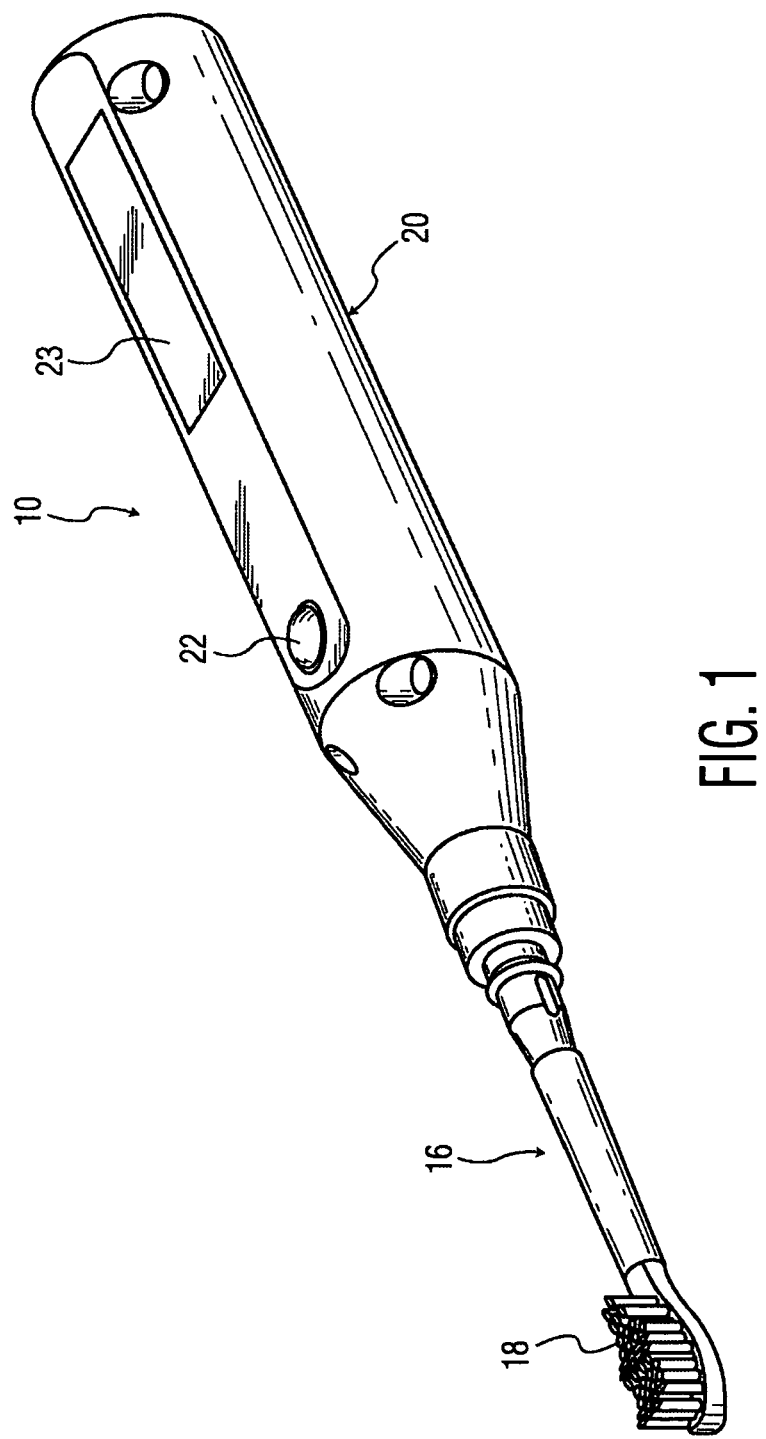
FIG. 1 is a perspective view of a toothbrush incorporating one embodiment of the present invention.
Figure 2:
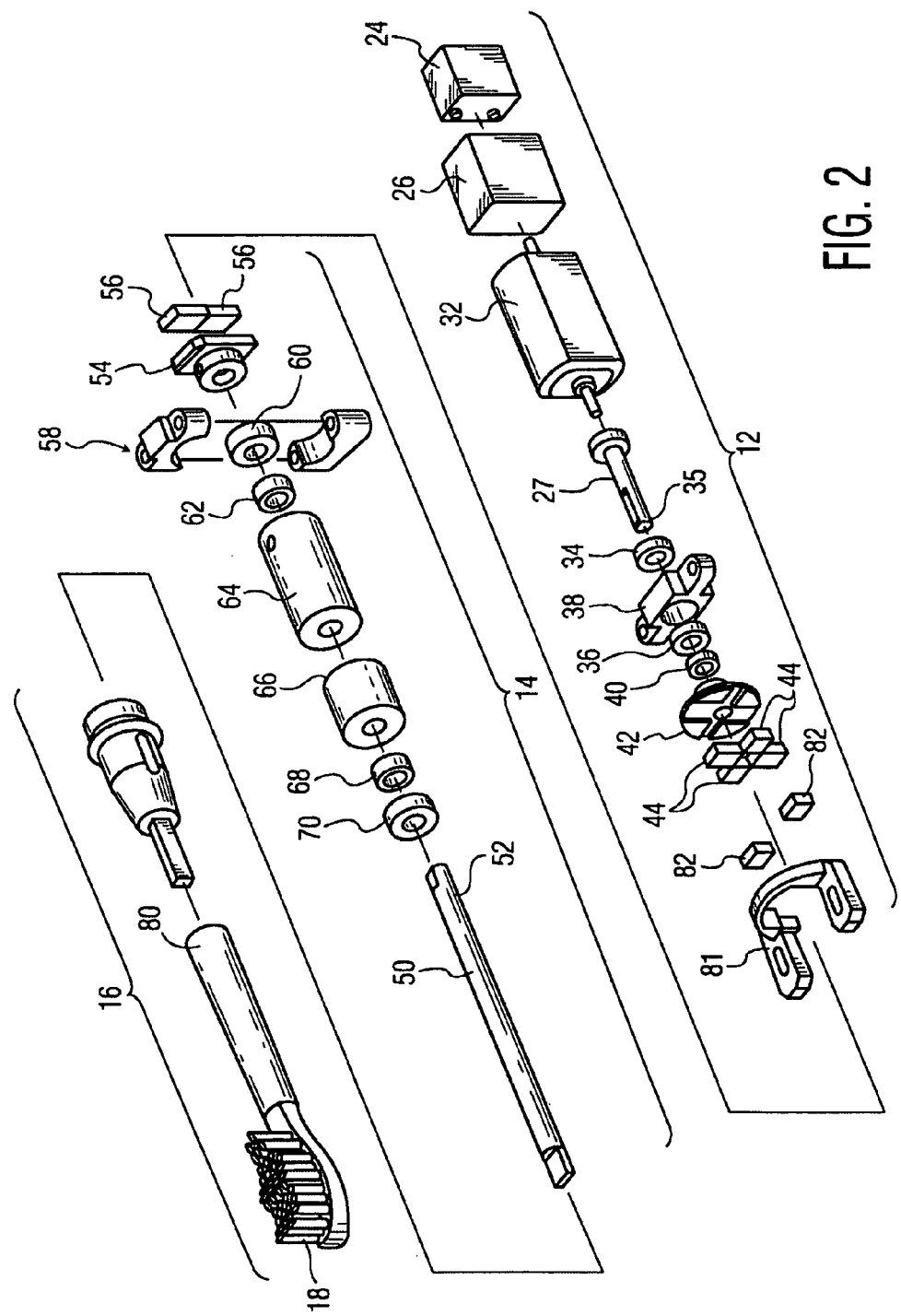
FIG. 2 is an exploded view of one embodiment of the resonant operating device of the present invention.

Referring to FIGS. 1 and 2, an embodiment of the invention shown and described herein includes a toothbrush 10 with drive assembly 12 which could, for instance, include a DC motor, and a driven assembly 14, the drive assembly 12 and the driven assembly 14 being coupled by a magnetic coupling arrangement, a portion of which is in the drive assembly 12 and a portion of which is in the driven assembly 14. At the remote (outboard) end of driven assembly 14 is a workpiece assembly 16, which as an example could include a toothbrush 18, but which could include a large number of other workpieces which have a reciprocating motion.

The drive assembly 12 and driven assembly 14 in the embodiment shown are positioned in a hand-held housing 20, which includes an on/off button 22 and could include a display 23 for providing a visual representation of various operating aspects of the device. The drive assembly 12, shown in detail in FIG. 2, is powered by a battery 24 and a power control circuit 26. As explained in more detail below, operation of the device is initiated by on/off button 22. The frequency of the drive assembly output shaft will increase from startup until the resonant frequency of the driven system is reached, at which point the driven system is excited by energy from the drive system as it turns, reciprocating with an amplitude which produces an effective action for the particular workpiece operation, such as brushing teeth.

Referring still to FIG. 2 in particular, the present embodiment includes a DC motor 32. DC motor 32 can be a common, inexpensive, off-the-shelf motor, available from a variety of manufacturers. DC motor 32 is powered by battery 24, under the control of a power control circuit 26. DC motor 32 drives a motor shaft 27, the forward end 35 thereof being mounted by two bearings 34 and 36, which are positioned in a bearing block assembly 38. Bearings 34 and 36 are not necessary; they are used to take up the thrust load on the device. Bearing block assembly 38 is fixed to the housing 20 to aid in taking up the thrust force. Alternatively, bearing block assembly 38 could be fixed to the motor housing. Forward (toward the workpiece) of the bearing block assembly 38 is a collar 40 for support of shaft 27. Mounted on the forward end of motor shaft 27 is a four-pole hub 42.

The present embodiment has a magnetic coupling arrangement between the drive assembly and the driven assembly. Hub 42 has secured thereto at 90° spaced intervals four magnets 44 44. In the embodiment shown, the magnets are oriented N S N S polarity facing the air gap between the drive assembly and the driven system. It should be understood that other embodiments could have more or fewer individual magnets with other polarity arrangements, such as N N N N or S S S S, which provide different multiplier effects.

The magnets may be of different shapes, e.g. pie-shaped, or there could be a ring magnet, with alternating magnetic sections. In one arrangement, only one magnet, which extends across the entire hub surface, could be used. In operation, as the motor shaft 27 and hub 42 turn by operation of the DC motor 32, magnets 44 turn therewith. There is an air gap, typically on the order of 0.2 mm 6 mm between the drive assembly 12 and the driven assembly 19. It could be larger for non-oral healthcare devices.

Still referring to FIG. 2, the driven assembly 14 includes an elongated driven shaft 50. At the upstream end 52 (toward the motor) of the shaft 50 is a two-pole hub 54. Positioned in hub 54 with a 180° separation are two magnets 56 56, with a N N polarity orientation toward the air gap. There could be a different number and polarity arrangement of magnets 56, depending upon the particular embodiment. In one arrangement, a single magnet could be used, extending across the entire hub. Downstream of hub 54 (toward the workpiece) is a bearing block 58 and bearing 60 which supports driven shaft 50. Collar 62 also supports shaft 50. Mounted further downstream on shaft 50 is a helical spring 64 and a balance mass 66. The helical spring operates to provide a return force as shaft 50 rotates under the drive energy supplied by the drive assembly 12. Further downstream is another support collar 68 and a bearing 70, which also are conventional.

Workpiece assembly 16 is connected to the end of driven shaft 50. Assembly 16 includes a workpiece neck portion 80, onto the free end of which can be mounted a variety of workpieces, including a toothbrush assembly which, in the embodiment shown, includes a brushhead 18. There are many alternative workpieces which in operation have a reciprocating, i.e. vibrating, oscillating, etc., action, including various shavers, sanders, brushes, powered knives and a variety of reciprocating tools, as well as other personal care products and oral care products.

Figure 4:
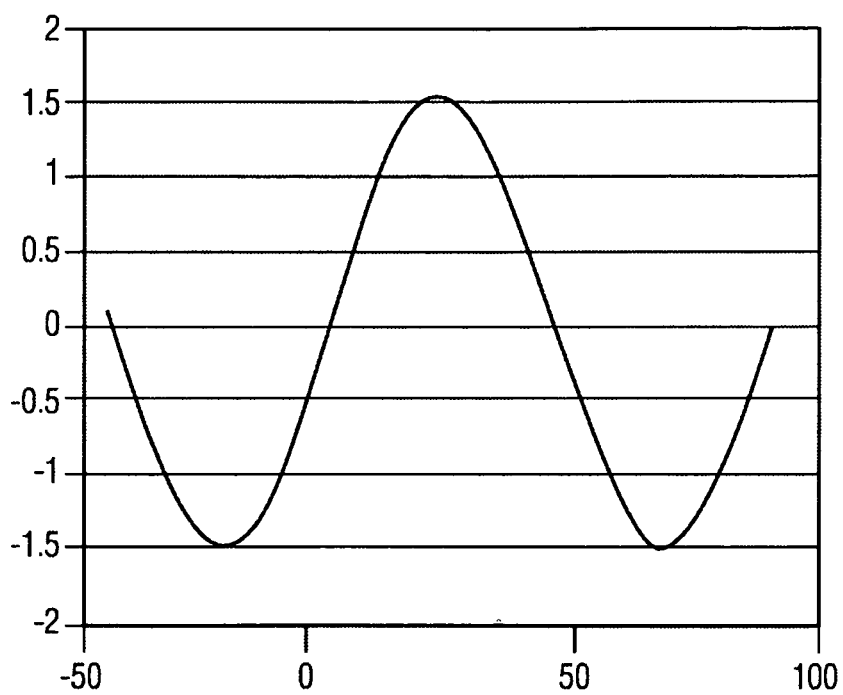
FIG. 4 is a diagram of torque v. time for the system of FIG. 1.

In operation of the embodiment of FIG. 2, the DC motor 32 will, upon actuation of the on/off switch 22, start up from 0 RPM. As drive magnets 44 pass the magnets 56 of the driven assembly in turn, torque, i.e. force, pulses will be generated. A force pulse in one direction from zero will be generated just before the passing of a driven magnet by a drive magnet and a force pulse in the other direction from zero will be generated just following the passing of a driven magnet. These could also be considered as two half pulses (each beginning at zero and ending at zero, in opposing directions, of a single pulse with plus and minus half portions. A force diagram is shown in FIG. 4, showing force against angular motion of the drive magnets. The force is at zero when the N (or S) polarity drive magnets are aligned with the driven magnets.

The number of full force pulses times (two half pulses) times the RPM of the motor is the drive frequency for the device. When the drive frequency is low, well below resonance, the amplitude of movement of the workpiece is quite small. As the frequency of the drive signal increases, due to increasing RPM of the motor as it comes up to operating speed, and in particular as it approaches resonance, typically within a few Hz thereof, the driven assembly will become excited by virtue of the resonance phenomenon, with the energy from the motor at that RPM transferring into the back-and-forth oscillation of the resonant system. The amplitude of the workpiece will increase significantly at this point, to an effective value, a clinically effective value for desired cleansing of teeth in the case of a toothbrush resonant system. The speed of the motor will change very little even though the motor is producing more torque, until the torque reaches a point which is sufficient to increase the drive frequency beyond resonance, referred to as overrun. There is, somewhat surprising, a significant window of operation where increasing energy from the driven system, after the near resonance value is reached, goes into amplitude. It is not, again surprisingly, a narrow range of operation. This is referred to as a "lock-in" range of operation.

Figure 7A:
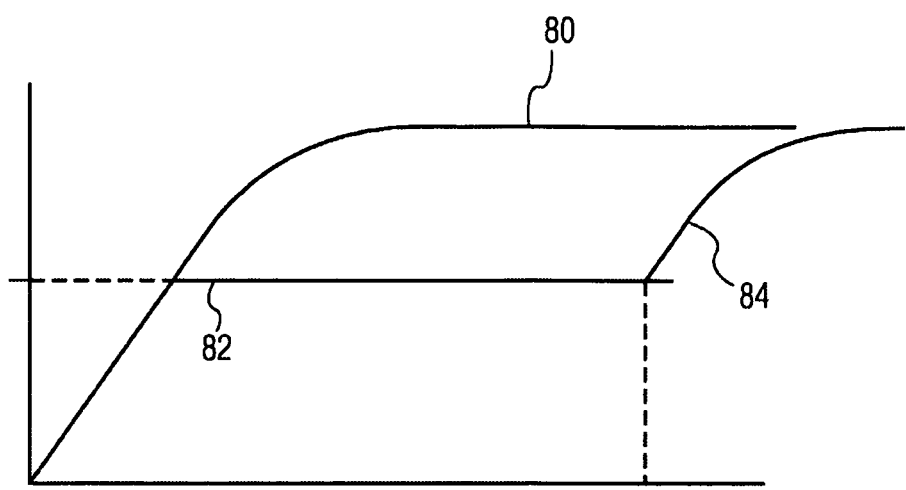
FIGS. 7A and 7B are graphs of motor speed and workpiece amplitude v. time from startup for operation of the system of FIG. 1.
Figure 7B:
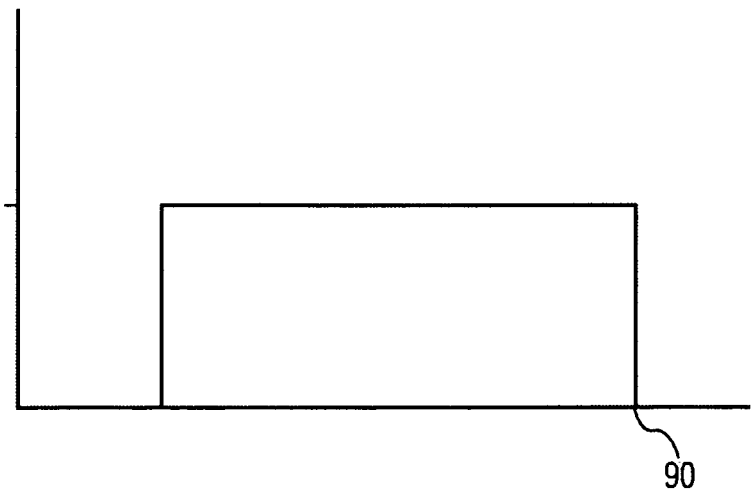

An important advantage of the present system is its ability to automatically adapt to changes in the resonant frequency of the driven system over time. FIG. 7A shows a graph of speed (RPM) of the drive v. time. The speed of the motor will increase over time in a non-resonant system until it reaches a maximum speed (as shown at 83). In a resonant system, the speed will increase to approximately resonance, as shown at 85, and will not increase further until sufficient value of torque is achieved that it goes into an overrun condition, shown at 87. FIG. 7B shows amplitude of movement of the workpiece for the resonant system relative to the speed/time graph of FIG. 7A. At the point of overrun 90, the amplitude will decrease significantly.

The present arrangement, as mentioned above, has the advantage of being able to automatically adapt to changes in the resonant frequency of the driven system, such as caused by aging, or can adapt automatically to different workpieces, e.g. different toothbrush heads. All of this is done automatically within the system as shown, without any electronic control.

When the device is operating approximately at resonance, further increases of amplitude may be accomplished through use of the power control circuit 26, which may be in the form of a slide switch or rotary element or other operator-actuated means, and which controls the application of battery power to the motor.

The magnetic coupling can be arranged so that there is a multiplier effect between the RPM of the motor and the drive frequency. This allows the motor to run at its most efficient speed. For instance, the arrangement specified above (N S N S) for the drive magnets and N N for the driven magnets produces a 2 1 advantage (drive frequency/motor RPM). Other polarity arrangements produce other multiplier effects, as is clear to one skilled in the art; for instance, a N N N N drive magnet arrangement with a N N (180° apart) driven magnet arrangement produces a 4 1 advantage.

The present embodiment also includes structure for startup of the device. Typically, in a rest position, the magnets of the drive assembly will be aligned with magnets of the driven assembly. In this position, a relatively high force is needed to start the rotation of the drive hub, overcoming the magnetic force between the drive and driven magnets. FIG. 2 shows a startup arrangement, which includes a starting block 81 which is positioned slightly downstream and separated from drive assembly hub and magnets 44. Starting block 81 is secured to the housing 20 of the device.

Positioned on a hub face of starting block 81 are two magnets 82 82 positioned 180° apart and orthogonal to magnets 56 56 in the driven assembly, the magnets having an N N polarity facing the air gap. These two startup magnets, also referred to as balance magnets, with opposing polarity relative to their counterpart magnets on the drive hub, produce approximately a net zero magnetic force between the two hubs, resulting in a low force startup/rotation for the hub 42. This is only one example of a startup arrangement; other startup arrangements which reduce the force necessary to accomplish startup would be clear to one skilled in the art.

The arrangement of FIG. 2 produces in operation a rotation of the driven assembly over a selected arc. It should be understood, however, that other modes of movement of the driven assembly can be accomplished. The driven assembly, can be mounted so as to produce an axial (in-and-out) motion, as well as a back-and-forth, i.e. side-to-side, motion. Other motions may also be possible, depending on the mounting of the driven assembly.

Further, two modes of motion of the driven assembly can be excited at the same time. For instance, if the axial mode resonant frequency is a harmonic of the resonant frequency of either the rotational or side-to-side mode, a single drive frequency can excite the driven assembly in both modes, resulting in a combined motion, for instance, a figure eight. Hence, depending upon the particular resonant frequencies of the various modes of movement of the driven assembly, a variety of workpiece movements can be produced. This is an advantage of the system of the present invention.

Furthermore, in toothbrush applications, for instance, it is possible to use the magnetic field produced by the drive system to drive a pump for gel or oral medication, in addition to moving an application such as a brushhead in one or two modes. Further, a mechanical takeoff from hub 42 or the motor driveshaft or the back end of the motor can be used to drive a pump or other element, such as a fan.

With respect to the drive system, it should be understood that a motor arrangement other than a DC motor could be used to drive the magnetic coupling arrangement. These could include turbine motors, air motors, spring assemblies, flywheels and hydraulic motors, among others. In addition, it should be understood that a magnetic coupling, while convenient and efficient, is not necessary. Other coupling arrangements or particular motors, such as a cogging motor, which produce drive pulses to a driven assembly, could be used, the drive frequency being controlled so as to increase from zero, so that again the drive frequency seeks out the resonant frequency of the driven assembly.

Other drive assembly alternatives include a motor with an eccentric member and a torsion bar, having a side-to-side mode of movement. The driven system will speed up to resonance, but will not go past resonance. Another alternative includes a lobbed cam on the motor drive shaft, with a cam follower with a spring. The brushhead is attached to the motor housing, producing a "cogging effect" reaction force in operation. Two discs could also be used, with different friction (viscous) areas. A varying force is transferred as the two discs move relative to each other.

Figure 8:
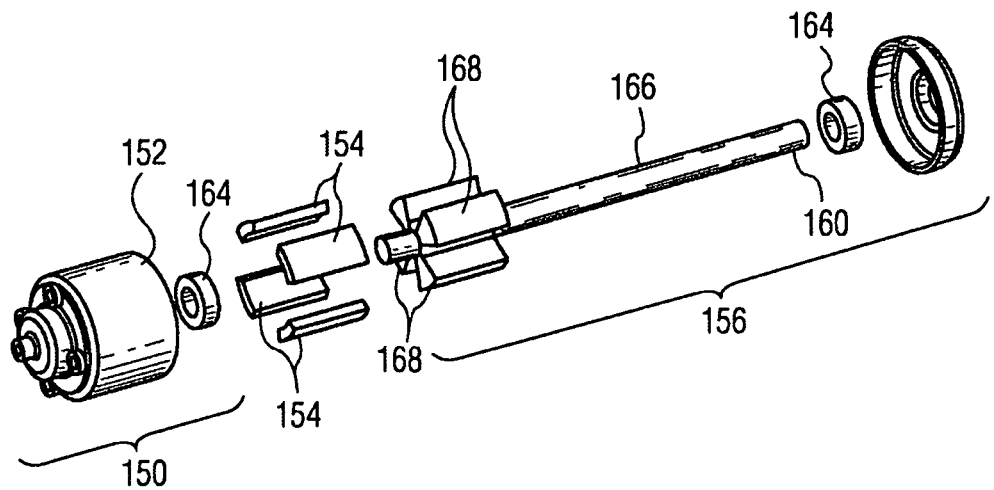
FIGS. 8-10 are exploded views of portions of alternative embodiments of the present invention.

FIG. 8 shows another magnetic coupling arrangement involving a cylindrical configuration. This embodiment includes a motor and hub 150 driven by a motor (not shown), hub 150 including a cylindrical housing 152. A plurality of magnets 154 154 are secured to an interior surface of the cylindrical housing 152. Magnets 154-154 are selected and arranged to create the desired number of force pulses per revolution.

A workpiece end hub 156 includes an armature shaft 158 on the free (outboard) end 60 of which is positioned a workpiece, such as a brushhead for a toothbrush. Shaft 158 is supported by bearings 164-164. At the inboard end of armature shaft 158 are a plurality of laminations (steel or iron) 168 which are mounted around the armature shaft 158. The coupling system shown will operate with or without magnets or laminations 168-168. However, placing magnets on the exposed ends of laminations 168 produces a greater torque in the magnetic coupling at the brush side of the system.

Figure 9:
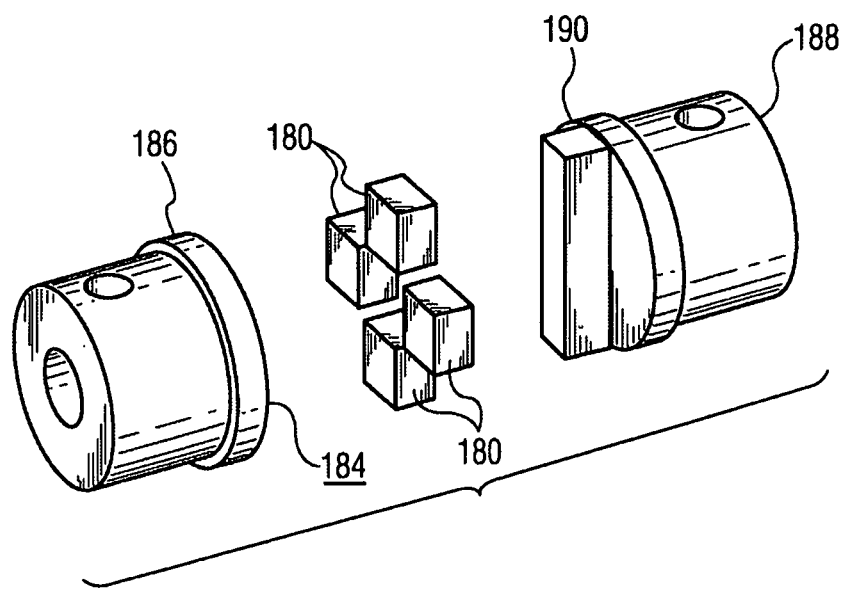

Another coupling embodiment involves reluctance. In this arrangement, shown in FIG. 9, a plurality of magnets (four orthogonal magnets 180-180) are shown mounted on an end surface 184 of drive and hub 186, which is rotated by the action of a motor (not shown). The brush end hub 188, which drives a brush arm and a brushhead, or other workpiece, includes a single carbon steel lamination 190 instead of a magnet or magnets. This arrangement produces a reluctance coupling between drive hub 186 and brush hub 188, to produce the desired turning action of hub 188 and the workpiece. Other magnet/lamination arrangements can of course be used. The magnets/laminations can be different shapes, such as pie-shaped, or could be a ring. The brush side lamination will match the shape of the drive hub magnets.

Figure 10:
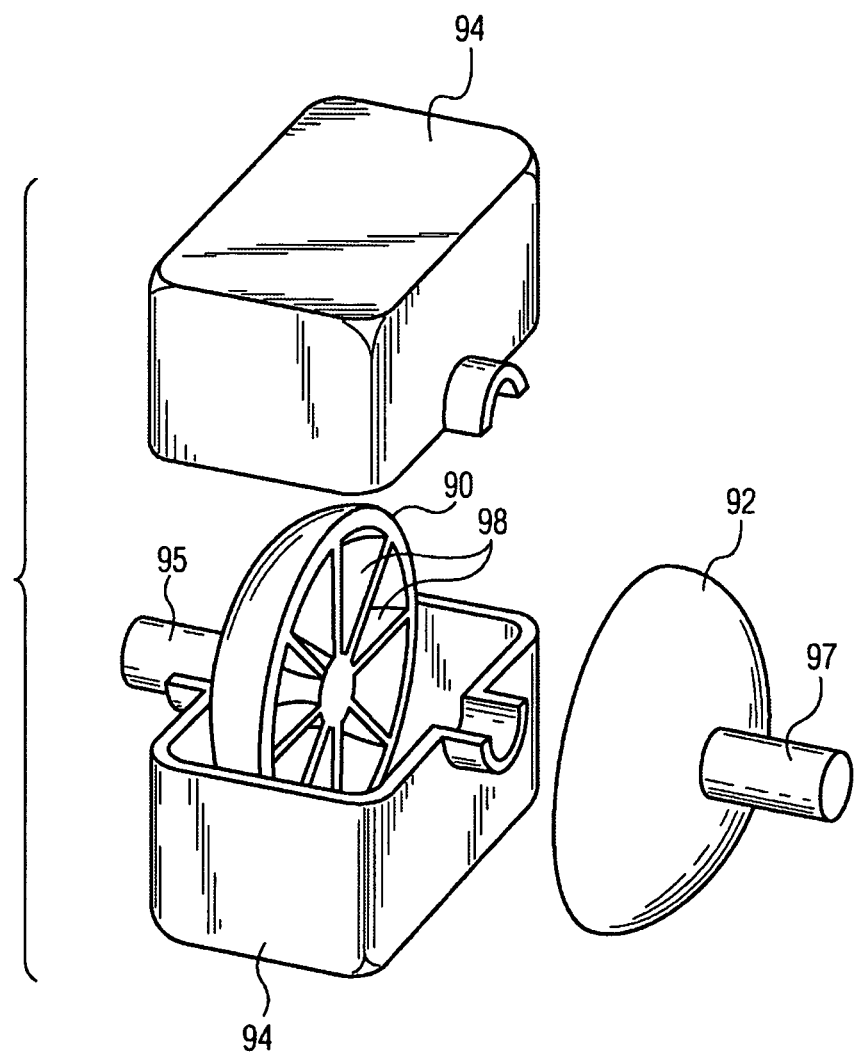

FIG. 10 shows a simplified arrangement of a viscous/cogging coupling system, referred to briefly above. The coupling structure includes two separate dish-shaped disc members 90 and 92, which are mounted in a housing 94, which is in turn filled with a viscous fluid. One of the discs, i.e. disc 90, is mounted on or part of a drive hub 95, driven by a motor (not shown), while the other disc, i.e. disc 92, is mounted to a brush hub shaft 97, on the end of which is mounted a workpiece member, such as a brushhead. The discs 90 and 92 are curved relative to the shafts 95, 97 on which they are mounted, as shown, and are positioned in the housing such that there is a small air gap between them. The discs 90 and 92 each have, respectively, a plurality of spaced interior vanes 98, equally spaced in the embodiment shown. Driving one of the discs, e.g. disc 90, by a motor will cause the other disc 92 to follow. A torque pulse is produced in the second disc when the vanes in the respective discs pass one another. The resulting series of torque pulses produces the same operational results as the magnetic coupling arrangement described in detail above. The effect of the viscous arrangement will increase with the relative speed of the discs, which results in an increase in shear rate in the fluid between them. This arrangement does not have a starting torque to overcome.

In the various arrangements shown and described, the article may include a display 23 for a number of different functions, including a timer for use of the device, a pressure meter, where pressure can be determined, and a battery charge status indicator. In addition, in the toothbrush embodiment, information can be provided to a user from sensors within the brushhead. A low power indication can also be displayed.

Figure 3:
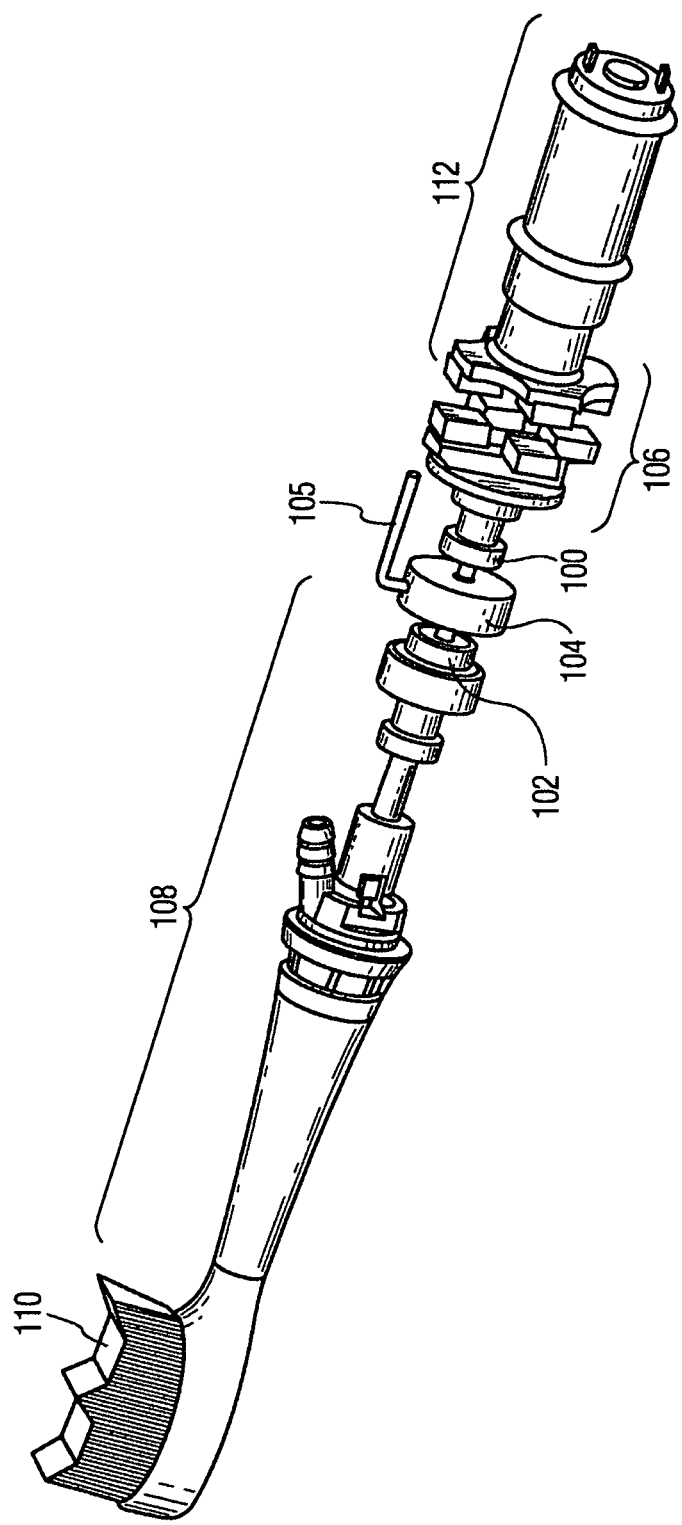
FIG. 3 is a diagram of an alternative embodiment of FIG. 2.

FIG. 3 shows a variation of the system of FIG. 2, in which the driven assembly is nodally mounted. In this embodiment, instead of the helical spring and balance mass, the spring assembly includes two torsion springs 100 and 102, which are positioned in series to provide a mechanically resonant rotating mechanism. The joint between the torsion springs is a "node" element 104 which remains substantially stationary. Node element 104 does not move or moves very little during operation of the system. Torsional spring 100 and the portion of the driven assembly upstream (toward the drive assembly) rotates in one direction, while torsional spring 102 and the downstream portion 108 of the driven assembly rotates in the other direction. This reduces the vibration of the driven assembly.

Reference is made relative to this embodiment to U.S. Pat. No. 6,859,968, owned by the assignee of the present invention, the contents of which are hereby incorporated by reference. A centering spring member 105, along with the node element 104, provide the centering force for the driven assembly, including the brush element 110 (or other workpiece). The centering spring member 105 is connected to the housing. In this embodiment, the drive assembly 112, including the motor and the magnetic drive hub, remains the same as for the other embodiment.

The starter or balance magnets described above can also be used to drive other functions in the drive train.

With the nodal mount drive that has a counter-rotation on the brush side (downstream side) from the driven side (upstream side), a rigid coupling can be used from the balance magnets to the brush side. This would add an impulse to the brush side equal and opposite the impulse from the driven side that matches the motion of the nodal mount. The balance magnets would in this case not be mounted to the handle or motor housing.

They could also be attached to a separate resonant system grounded to the motor or handle housing, with a resonant frequency just above the frequency of the driven system. This would allow the motor to lock into this resonant frequency in the case of excessive loading and overshoot, preventing the motor from continuing to speed up, effectively stopping overshoot. When the excessive load is relieved, the motor could then lock into the driven system resonant frequency as it drops back below that of the balance magnet resonant system. This would add an increase n handle vibration when overloaded that could be a feedback to the user.

The balance magnets could also be attached to some separate function assembly with its own resonant system tuned to the primary resonant system. This could drive other functions such as pumping, counter brush motion, etc.

Figure 5:
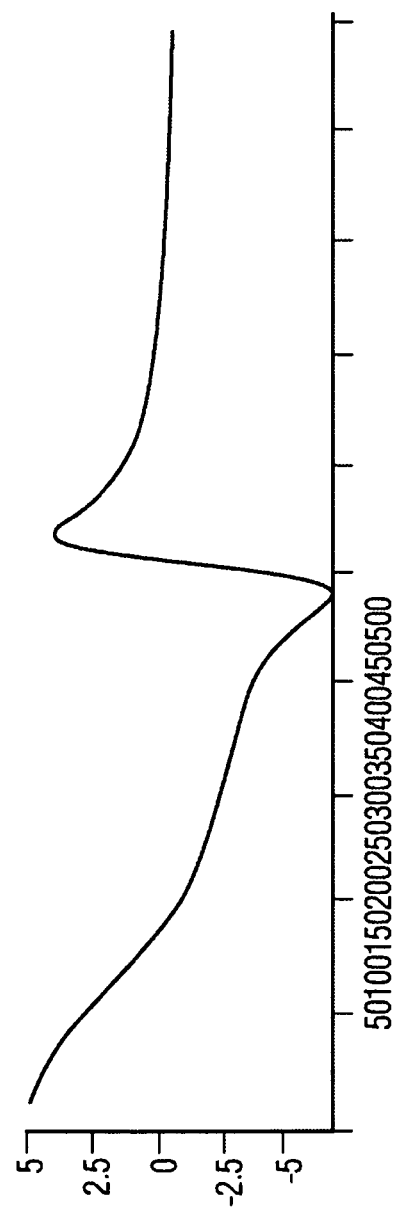
FIGS. 5 and 6 are diagrams of impedance and power transfer v. frequency for the system of FIG. 1, which has a resonant frequency of approximately 260 Hz.

In operation of the present system, the impedance of the driven assembly rapidly decreases as the frequency of the drive signal from the driven assembly approaches the mechanical resonant frequency of the driven assembly, as shown in FIG. 5. This sudden decrease in impedance near resonance indicates how the energy from the motor produces a significant increase in amplitude over a short period of time. The driven assembly becomes excited as the impedance decreases due to the power in the force pulses being transferred to the workpiece, thereby increasing the amplitude of movement of the workpiece significantly. Thus, until the drive frequency comes close to resonance, the amplitude is quite small. As the frequency gets close to resonance, small increases in frequency result in large changes in amplitude. FIG. 5 illustrates the change in impedance against torque. When the applied torque is sufficient to increase the operating frequency of the device above the region of resonance, the impedance of the driven assembly begins to rise rapidly.

Figure 6:
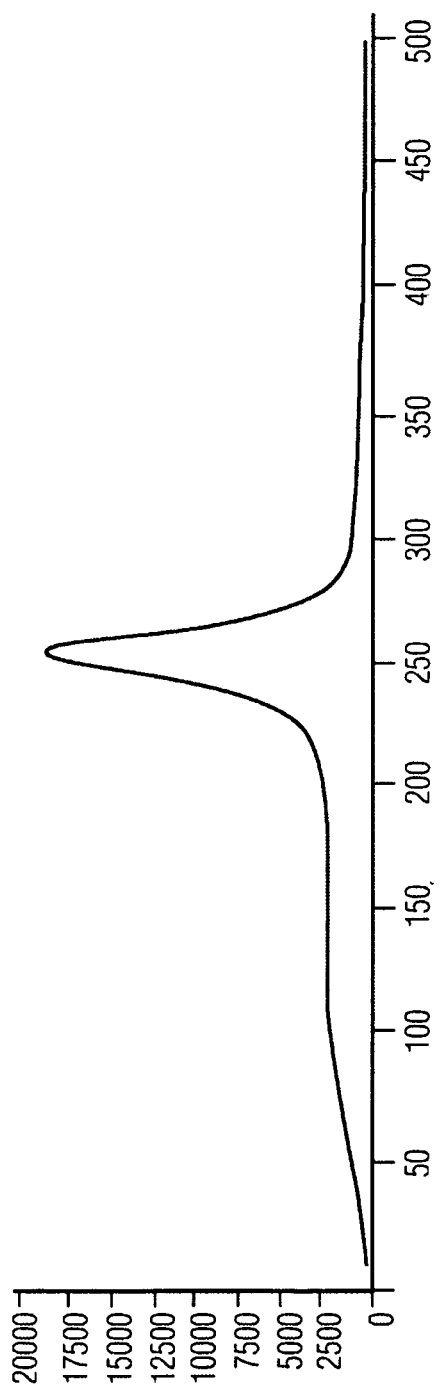

FIG. 6 shows the relatively narrow band of drive frequencies over which a large amount of the power in the force pulses are transferred to the workpiece for movement thereof. It is important, as indicated above, to prevent "overrun" by the motor by ensuring that there is insufficient torque in the motor to get past the resonant frequency. When the system is operating correctly, the power transfer to the workpiece and the resulting amplitude of the workpiece is high, while the impedance of the driven system is at a minimum.

The system described above operates typically at a frequency which is slightly below resonance. The frequency of the drive system increases from zero to that point. Alternatively, it may be possible for the drive frequency to initially overshoot or go beyond resonance and then "fall back", i.e. decrease, until the near resonance point is reached, at which the transfer of energy to amplitude of workpiece movement occurs.

There are several advantages to the system of the present invention, including simplified electronics (or no electronic control) control, low vibration and low noise of the device during operation. It has a relatively small size, high efficiency and is easy to clean. Most importantly, however, it eliminates the tuning and tolerance manufacturing and quality control requirements of normal resonant systems.

It also permits a very simple, inexpensive, yet effective, power toothbrush, involving for instance a motor, battery, on-off switch and magnetic coupling, without electronic control, yet still achieving desired cleansing effects, with a brushhead velocity of greater than 1.5 meters per second and operation of frequency and amplitude in the ranges set out in U.S. Pat. No. 5,378,153.

Although a preferred embodiment of the invention has been disclosed for purposes of illustration, it should be understood that various changes, modifications and substitutions may be incorporated in the embodiment without departing from the spirit of the invention which is defined by the claims which follow.

What is claimed is:

1. A workpiece system having a reciprocating action, comprising:
    a drive assembly coupled with a driven member assembly in such a manner to produce a drive signal for the driven assembly comprising periodic force pulses, resulting in a drive frequency which increases from zero in operation of the work piece system; and
    a driven member assembly having a workpiece mounted thereon with a return action assembly, the driven member assembly having a resonant frequency, wherein, as the drive frequency increases from zero as the periodic force pulses increase, the drive frequency will approach the resonant frequency of the driven assembly, wherein at approximately said resonant frequency, at least a substantial portion of energy produced as a result of the force pulses is transferred into the movement of the workpiece, producing an effective workpiece action.

2. The system of claim 1, wherein further increases in energy produced by the drive assembly at said approximately resonant frequency are transferred into movement of the workpiece, for a range of increase in energy, thereby locking in energy increases to increases in workpiece movement.

3. The system of claim 1, wherein the drive assembly includes a DC motor with an output shaft which rotates in operation.

4. The system of claim 3, wherein the system includes a magnetic coupling arrangement between the drive system and the driven system.

5. The system of claim 4, wherein the drive system includes a first hub member attached to the output shaft from the DC motor and at least one magnet mounted on a forward surface thereof, and wherein the driven system includes a second hub member mounted on a driven system shaft and at least one magnet mounted on a rear surface thereof, such that as the first hub member rotates, the magnet thereon slips past the magnet on the second hub, producing force pulses to the driven system.

6. The system of claim 5, including a plurality of magnets on the first hub member and a plurality of magnets on the second hub member.

7. The system of claim 4, wherein the drive system includes a first hollow cylindrical hub member attached to the output shaft from the DC motor and a plurality of magnets mounted on an internal surface thereof, and wherein the driven system includes a second cylindrical hub member which fits into the first hub member, the second cylindrical hub member including armature elements which result in coupling between the first and second hubs in operation.

8. The system of claim 7, including magnets positioned on the armature elements.

9. The system of claim 8, wherein the modes of movement include both axial and rotational movement.

10. The system of claim 3, including a power control assembly providing an adjustable level of power to the motor, thereby providing the capability of changing the amplitude of movement of the workpiece assembly when the system is operating at approximately resonance.

11. The system of claim 1, wherein the workpiece is a personal care device.

12. The system of claim 11, wherein the oral care device is a toothbrush.

13. The system of claim 1, wherein the workpiece is an oral care device.

14. The system of claim 1, wherein the drive system includes a first hub member attached to the output shaft from the DC motor and at least one magnet mounted on a forward surface thereof, and wherein the driven system includes a second hub member mounted on a driven system shaft and a steel member mounted on the driven system shaft, in operation producing a reluctance coupling between the drive and driven system.

15. The system of claim 1, wherein the system includes a viscous coupling assembly between the drive system and the driven system, the viscous coupling assembly including first and second members with spaced vanes, facing each other in a housing with a viscous fluid, such that as the drive system moves one member with vanes, movement of the second member with vanes occurs by virtue of the vanes on the first member slipping past the vanes on the second member in the viscous fluid.

16. The system of claim 1, wherein the spring assembly includes a centering node element and two torsional springs on either side thereof operating in countermotion, wherein the node element is secured to a housing for the workpiece system.

17. The system of claim 1, wherein the spring assembly includes a torsional spring member and a balance mass, the torsional spring being secured to a housing for the workpiece system.

18. The system of claim 1, wherein the driven assembly is mounted so as to have more than one mode of movement, and wherein the modes of movement and the resonant frequencies thereof are selected and determined that a single drive frequency can excite both modes of movement.

19. The system of claim 1, wherein the driven assembly is mounted so that the workpiece thereon rotates through a selected arc.

20. The system of claim 1, wherein the driven assembly is mounted so that the workpiece moves axially.

21. The system of claim 1, wherein the driven assembly is mounted so that the workpiece moves back and forth through a selected arc.

22. The system of claim 1, including means using the action of the drive assembly for pumping a fluid to the workpiece in addition to moving the driven assembly.

23. The system of claim 1, wherein the system adapts automatically to changes in the resonant frequency of the driven assembly over time.

24. The system of claim 1, wherein the drive system is adapted to drive other elements besides said driven system on which a workpiece is mounted.

25. The system of claim 1, wherein the workpiece is a toothbrush.

26. The system of claim 1, wherein the system adapts automatically to changes in the resonant frequency of the driven assembly, including change of the workpiece.

27. A dental hygiene device for cleaning teeth, comprising:
a drive assembly coupled with a driven assembly in such a manner to produce a drive signal for the driven assembly comprising force pulses, resulting in a drive frequency which gradually increases from zero in operation of the dental hygiene device, wherein the drive assembly includes a battery powered DC motor; and
the driven assembly having a brushhead mounted thereon with a return spring assembly, the driven assembly having a resonant frequency, and wherein as the drive frequency increases from zero, the drive frequency will approach the resonant frequency of the driven assembly, at which point the energy produced by the motor is transferred into movement of the brushhead, such that the tips of the bristles of the brushhead move at a velocity greater than approximately 1.5 meters per second, sufficient to produce a cleansing action on the teeth.

28. The device of claim 27, characterized by a lack of electronic control elements, except for an on-off switch.

29. The device of claim 27, wherein the batteries are replaceable.

* * * * *